(12) United States Patent
Yuasa

(10) Patent No.: US 8,836,951 B2
(45) Date of Patent: Sep. 16, 2014

(54) IMAGING DEVICE FOR OPTICAL COHERENCE TOMOGRAPHIC IMAGE AND IMAGING METHOD

(75) Inventor: Takashi Yuasa, Sagamihara (JP)

(73) Assignee: Canon Kabushiki Kaisha, Tokyo (JP)

( * ) Notice: Subject to any disclaimer, the term of this patent is extended or adjusted under 35 U.S.C. 154(b) by 252 days.

(21) Appl. No.: 13/320,740

(22) PCT Filed: May 20, 2010

(86) PCT No.: PCT/JP2010/003384
§ 371 (c)(1),
(2), (4) Date: Nov. 15, 2011

(87) PCT Pub. No.: WO2010/134342
PCT Pub. Date: Nov. 25, 2010

(65) Prior Publication Data
US 2012/0057168 A1    Mar. 8, 2012

(30) Foreign Application Priority Data

May 22, 2009   (JP) .................................. 2009-124273
Mar. 23, 2010  (JP) .................................. 2010-066729

(51) Int. Cl.
| G01B 11/02 | (2006.01) |
| A61B 3/12 | (2006.01) |
| G01B 9/02 | (2006.01) |
| A61B 3/10 | (2006.01) |
| A61B 5/00 | (2006.01) |

(52) U.S. Cl.
CPC .............. *A61B 3/12* (2013.01); *G01B 9/02091* (2013.01); *G01B 9/02067* (2013.01); *A61B 3/102* (2013.01); *A61B 5/0059* (2013.01); *A61B 5/0066* (2013.01); *A61B 5/0075* (2013.01); *A61B 5/441* (2013.01)

USPC .......................................................... 356/497

(58) Field of Classification Search
USPC ................ 356/479, 497; 250/227.19, 227.27
See application file for complete search history.

(56) References Cited

U.S. PATENT DOCUMENTS

| 7,263,394 B2 * | 8/2007 | Wang ............................ 600/316 |
| 7,936,462 B2 * | 5/2011 | Jiang et al. .................... 356/497 |
| 8,427,653 B2 * | 4/2013 | Hacker et al. ................. 356/497 |
| 2008/0175465 A1 | 7/2008 | Jiang |
| 2010/0280315 A1 * | 11/2010 | Pan .............................. 600/109 |

FOREIGN PATENT DOCUMENTS

| CN | 101115436 A | 1/2008 |
| JP | 2008-508068 A | 3/2008 |
| JP | 2008-520992 A | 6/2008 |
| WO | 2006-015717 A2 | 2/2006 |
| WO | 2006-054116 A1 | 5/2006 |

* cited by examiner

*Primary Examiner* — Michael A Lyons
(74) *Attorney, Agent, or Firm* — Canon U.S.A., Inc., IP Division

(57) ABSTRACT

The present invention relates to an imaging device including a reducing section configured to reduce superimposition of first and second combined lights upon each other. The first and second combined lights are based on first and second measuring lights that illuminate an examination object. The imaging device according to the present invention also includes an obtaining section configured to obtain an optical coherence tomographic image of the examination object based on the first and second combined lights whose superimposition has been reduced at the reducing section. A sensor having a minimum number of pixels is provided by restricting crosstalk between interference lights at the sensor.

30 Claims, 7 Drawing Sheets

PORTIONS WHERE NOISE COMPONENTS OVERLAP

IMAGING DEVICE FOR OPTICAL COHERENCE TOMOGRAPHIC IMAGE AND IMAGING METHOD

TECHNICAL FIELD

The present invention relates to an imaging device using optical coherence tomography, an imaging method, and medical equipment used in observing, for example, the fundus of an eye or skin.

BACKGROUND ART

In recent years, an imaging device (hereunder may also be referred to as an "OCT device") using optical coherence tomography (OCT) making use of coherence of low coherence light has been put into practical use. Since it is possible to obtain a tomographic image at a resolution of an order of a wavelength of light that is incident upon a sample, the tomographic image of the sample can be obtained with high resolution.

In particular, in obtaining a tomographic image of a fundus/retina in the ophthalmologic field, the OCT device is becoming an indispensible device. Even outside the ophthalmologic field, tomographic observation of the skin and tomographic imaging operation of a wall of a circulatory organ or a digestive organ using the OCT device as an endoscope or a catheter are carded out.

Here, two types of OCT method are primarily available, that is, time domain-OCT (TD-OCT) and Fourier domain-OCT (FD-OCT). The FD-OCT is a method in which spectrum information of interference light is subjected to Fourier transformation, to obtain together pieces of intensity information corresponding to depth-direction positions. Therefore, the FD-OCT can obtain a tomographic image at a higher speed than the TD-OCT in which a coherence gate position is changed for obtaining a depth-direction position.

In the OCT device, when making measurements at a high resolution, a measurement area per beam becomes narrow, as a result of which a relatively large amount of measurement time is required. In particular, when the OCT device is used in ophthalmology, imaging operations are required to be performed at high speeds. This is because images may be displaced from each other by, for example, involuntary eye movement during the imaging operation.

PCT Japanese Translation Patent Publication No. 2008-508068 (Patent Literature 1) discusses a method that uses a plurality of beams and that narrows a measurement area per one beam to reduce the measurement time.

In the Patent Literature 1, an interferometer that separates nine beams into measuring lights and reference lights is used. Interference lights obtained from the respective beams are dispersed, and the dispersed interference lights are detected same two-dimensional sensor array for the plurality of beams.

CITATION LIST

Patent Literature

PTL 1: PCT Japanese Translation Patent Publication No. 2008-508068

SUMMARY OF INVENTION

By, for example, thermal flickering of a light source itself, light generated from the light source generates light having wavelength widths that are larger than an intended wavelength width.

Therefore, in the PTL 1, in order to prevent a plurality of dispersed interference lights from being superimposed upon each other on the two-dimensional sensor array, the distances between areas where the respective interference lights are detected are made sufficiently large. This is because, when the plurality of interference lights are superimposed upon each other on the sensor, crosstalk occurs between the interference lights, thereby generating noise in a resulting tomographic image that is obtained.

Here, since it is necessary for the detection areas to be sufficiently separated apart from each other, pixels that are not used for the detection are provided. Therefore, the number of pixels required for the two-dimensional array sensor is increased, thereby reducing read-out speed.

An imaging device according to the present invention includes an illuminating section configured to illuminate an examination object with first and second measuring lights; a detecting section configured to detect a first combined light based on the first measuring light and a second combined light based on the second measuring light; a reducing section configured to reduce superimposition of the first and second combined lights upon each other at the detecting section; and an obtaining section configured to obtain an optical coherence tomographic image of the examination object based on the first and second combined lights whose superimposition has been reduced at the reducing section.

An imaging method according to the present invention includes the steps of illuminating different positions of an examination object with measuring lights formed of a plurality of lights;

combining returning lights and reference lights formed of a plurality of lights, the returning lights corresponding to the measuring lights, formed of the plurality of lights, that are reflected or scattered by the examination object;

detecting interference lights, formed by the combining of the returning lights and the reference lights, with a sensor;

reducing a light quantity of a portion where a first interference light and a second interference light adjacent to the first interference light are superimposed upon each other at the sensor that receives the interference lights; and obtaining an optical coherence tomographic image of the examination object.

According to the present invention, the light quantity resulting from the plurality of dispersed lights being superimposed upon each other at a sensor is reduced. By this, it is possible to prevent crosstalk from occurring between the dispersed lights on the sensor. In addition, it is possible to bring areas (unit: pixels) where the plurality of lights illuminate the sensor towards each other.

Further features of the present invention will become apparent from the following description of exemplary embodiments with reference to the attached drawings.

DESCRIPTION OF EMBODIMENTS

Figure 1A:
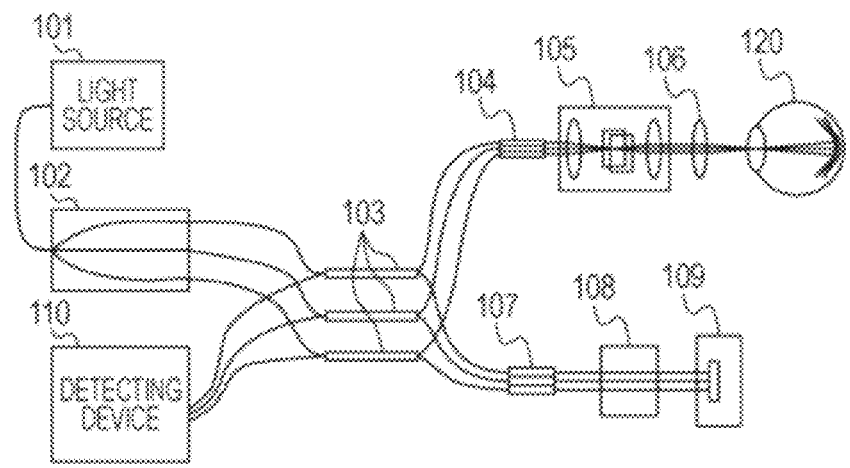
FIG. 1A is schematic view illustrating, for example, the structure of an imaging device using optical coherence tomography according to a first embodiment.

An imaging device (which may also be called an "imaging device using optical coherence tomography") according to an embodiment of the present invention will be described with reference to FIGS. 1A and 1B.

First, reference numeral 101 denotes a light source for generating light (low coherence light). A super luminescent diode (SLD) can be applied to the light source 101. Amplified spontaneous emission (ASE) can also be applied to the light source 101. In addition, ultrashort pulse laser, such as titanium sapphire laser, can also be applied to the light source 101. Anything that can generate low coherence light may be applied to the light source 101. The wavelength of the light generated from the light source 101, though not particularly limited, is in the range of from 400 nm to 2 [micro]m. A wavelength interval for realizing OCT may be, for example, 1 nm or more; desirably, 10 nm or more; and, more desirably, 30 nm or more.

Reference numerals 103 denote splitting sections that split the light from the light source 101 into reference lights and measuring lights. For example, a beam splitter or a fiber coupler may be applied to the splitting sections 103. Accordingly, anything that can split the light may be applied to the splitting sections 103.

Reference numeral 105 denotes a scanning optical section (which may also be called a "scanning section") for scanning an examination object to be examined 120 with the measuring lights. For example, a galvano scanner is desirably used for the scanning optical section 105. However, anything that can scan an examination object with light may be used.

Reference numeral 110 denotes a detecting section (spectroscope) for detecting combined lights of the reference lights and returning lights from the examination object 120. The detecting section 110 includes a dispersing element 114 (which may also be called a "dispersing section") for dispersing a plurality of combined lights (117a, 117b, 117c). The dispersing element 114 is, for example, a diffraction grating or a prism, and may be anything that can disperse the light. The detecting section 110 includes a sensor 116 for detecting a plurality of dispersed lights (118a, 118b, 118c) dispersed by the dispersing element 114. The sensor 116 may be a line sensor, a two-dimensional sensor, or anything that can detect the light.

The examination object 120 can be scanned with the plurality of measuring lights used to scan the examination object 120. The method that a Michelson type interferometer uses for forming a plurality of measuring lights differs from the method that a Mach-Zehnder type interferometer uses for forming a plurality of measuring lights (described later).

The sensor 116 has first and second areas (for example, areas 119a, 119b, 119c) where first and second lights that have been dispersed (for example, lights 118a, 118b, 118c) are focused. Here, the first and second areas refer to areas (unit: pixels) where the sensor is irradiated with the plurality of dispersed lights. In a first embodiment described below, 1170 pixels where the dispersed lights are focused correspond to the first and second areas.

The device is formed so that, of the first lights (such as the light 118a), the quantity of light having a wavelength that can illuminate the second area (such as the area 119b) is reduced (that is, the light is intercepted or the light quantity is reduced). Alternatively, the device is formed so that the light quantity resulting from the plurality of dispersed lights being superimposed upon each other on the sensor 116 is reduced.

This makes it possible to restrict crosstalk between the dispersed lights in the sensor 116. In addition, the first and second areas can be brought as close as possible to each other. That is, the distances between the first and second areas (unit: pixels) can be made small (the number of pixels can be made small). This includes a state in which the distance is zero. In the first embodiment (described later), 132 pixels, provided between the first and second areas formed by the 1170 pixels, correspond to the distance.

The imaging device according to the embodiment includes an irradiating section (such as the scanning section) configured to irradiate an examination object with the first and second measuring lights. The imaging device according to the embodiment also includes a detecting section (such as the dispersing section) that detects first combined lights, which are based on first measuring lights, and second combined lights, which are based on second measuring lights. The first combined lights are formed by combining returning lights (returning from the examination object irradiated with the first measuring lights) with first reference lights corresponding to first measuring lights. The second combined lights are formed by combining returning lights (returning from the examination object irradiated with the second measuring lights) with second reference lights corresponding to second measuring lights. Further, the imaging device according to the embodiment includes a reducing section (such as an optical filter (described later)) that reduces the amount by which the first and second combined lights are superimposed upon each other at the detecting section. Still further, the imaging device according to the embodiment includes an obtaining section (no shown) that obtains an optical coherence tomographic image (which may also be called a "tomographic image") based on the first and second combined lights whose superposition amount has been reduced at the reducing section. Anything may be used for the obtaining section as long as it obtains a tomographic image by performing a signal processing operation such as Fourier transformation on data transmitted from the sensor of the detecting section.

Here, it is desirable that the imaging device include a light-quantity reducing member (which may also be called a "reducing section") for reducing the superposition amount. Here, as the light-quantity reducing member, it is desirable to use an optical filter 112 that is capable of limiting transmittance or reflectivity of light having a particular wavelength. Here, the optical filter 112 reduces the superposition amount of the plurality of combined lights (117a, 117b, 117c). The plurality of combined lights whose superposition amount has been reduced are dispersed by the dispersing element 114. As the light-quantity reducing member, it is desirable to use an intercepting member 410 that intercepts the plurality of the dispersed lights (118a, 118b, 118c).

It is desirable that the device be formed so that the plurality of dispersed lights (118a, 118b, 118c) are focused on the respective areas (119a, 119b, 119c).

Michelson Type Interferometer

First to Third Embodiments

If a Michelson type interferometer is used, the splitting sections 103 are formed so that the reference lights and the measuring lights are combined. That is, the splitting sections 103 are formed so as to split the light generated from the light source 101 into reference lights and measuring lights, and so as to combine the reference lights and returning lights.

Here, the splitting sections 103 split the light generated from the light source 101 into a plurality of lights, and split the plurality of split lights into reference lights and measuring lights (first and second embodiments).

Light is generated from a plurality of the light sources 910a, 910b, and 910c. Then, the plurality of lights are split into reference lights and measuring lights (third embodiment in which a plurality of light sources are provided).

Mach-Zehnder Type Interferometer

Fourth and Fifth Embodiments

If a Mach-Zehnder type interferometer is used, a combining section for combining the reference lights and the measuring lights is provided. The combining section is, for example, a fiber coupler 407 or anything else that can combine the lights.

Light generated from the light source 10 is split into the measuring lights and the reference lights, and the split measuring lights and the split reference lights are split into a plurality of lights.

Another Embodiment

Imaging Method

An imaging method using optical coherence tomography according to another embodiment of the present invention includes the following steps;
a) illuminating different positions of an examination object with measuring lights formed of a plurality of lights;
b) combining returning lights and reference lights formed of a plurality of lights, the returning lights corresponding to the measuring lights, formed of the plurality of lights, that are reflected or scattered by the examination object;
c) detecting interference lights, formed by the combining of the returning lights and the reference lights, with a sensor;
d) reducing a light quantity of a portion where a first interference light and a second interference light adjacent to the first interference light are superimposed upon each other at the sensor that receives the interference lights; and
e) obtaining a tomographic image (may also be called a "optical coherence tomographic image") of the examination object.

Here, in another embodiment, the imaging method using optical coherence tomography according to the above-described embodiment may be stored in a computer-readable storage medium (such as a flexible disc, a hard disk, an optical disk, a magneto-optical disk, a CD-ROM, a CD-R, a magnetic tape, a nonvolatile memory card, ROM, EEPROM, or Blu-ray Disc) as a program to be executed by a computer. A still another embodiment may be related to a program for executing by a computer the aforementioned method using optical coherence tomography.

Another Device Structure

A fiber beam splitter 102 splits light that has exited from a low-coherence light source 101 into a plurality of lights. Fiber couplers 103 further split the plurality of split lights into measuring lights and reference lights formed by the plurality of lights. Then, as mentioned below, the measuring lights are guided to an examination object (which is a measurement object), and the reference lights are guided to a reference mirror. When the measuring lights, formed by the plurality of lights, are guided to the examination object, the measuring lights are emitted from fiber collimators 104 that are arranged at a particular interval. The measuring lights, formed by the plurality of lights, used for scanning by a scanning unit (a scanning optical system) 105 for beam scanning illuminate a measurement object (examination object) 120 through an objective lens 106 constituting an illumination optical system. Returning lights, formed by reflection or scattering of the measuring lights at the measurement object 120, pass through the same optical system again and return to the fiber couplers 103. The reference lights exit from fiber collimators 107, are reflected by a reference mirror 109, and return to the fiber couplers 103. Here, for adjustment of a wavelength scattering amount with respect to the reference lights, the reference lights pass through a dispersion compensation glass. The measuring lights that have been scattered by the measurement object 120 and that have returned to the fiber couplers 103 and the reference lights that have been reflected by the reference mirror 109 and that have returned to the fiber couplers 103 are combined with each other at the fiber couplers 103, so that interference lights are formed. The interference lights, formed by combining the measuring lights and the reference lights at the fiber couplers 103 in this way, are detected as interference signals corresponding to the respective measuring lights by an interference-light detecting device 110.

Figure 1B:
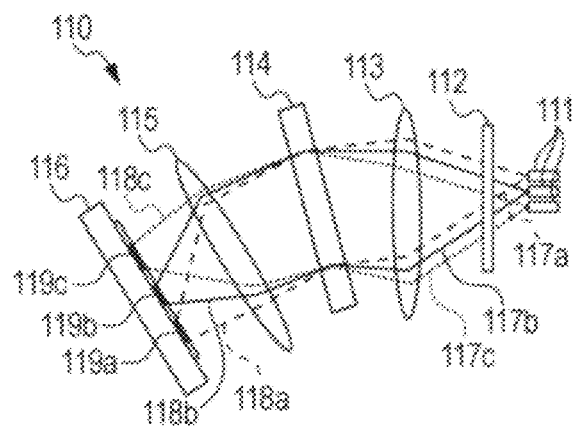
FIG. 1B is schematic view illustrating, for example, the structure of the imaging device using optical coherence tomography according to the first embodiment.

The interference-light detecting device 110 has the structure shown in FIG. 1B. The interference lights input by the fibers exit into the air from fiber ends 111 arranged at a particular interval, pass through an optical filter 112 (that passes only light having wavelengths of a particular wavelength range), and are formed into parallel lights by a collimator lens 113. The parallel lights pass through a dispersing element 114 (such as a prism or a diffraction grating), and are dispersed, that is, are subjected to wavelength separation. Then, the dispersed lights are focused on a sensor array 116 by a focusing lens 115. The input interference lights 117a, 117b, and 117c are dispersed, and are focused for respective wavelengths at different areas on the sensor array 116. At this time, a transmission wavelength band of the optical filter 112 is set so that the interference lights that are adjacent to each other are not superimposed upon each other (that is, so that crosstalk does not occur). That is, a portion of a long-wavelength-side light of one of the adjacent interference lights and a portion of a short-wavelength-side light of the other adjacent interference light are prevented from passing through the optical filter 112. Therefore, it is possible to efficiently obtain a plurality of interference signals without crosstalk. Data obtained at the sensor array 16 is subjected to a signal processing step including a Fourier transformation operation, and is converted into OCT data.

According to the structure of the aforementioned embodiment, adjacent interference lights can be disposed next to each other on the sensor array without crosstalk. Therefore, interference signals corresponding to a plurality of beams can be detected using a minimum number of sensor array pixels. Consequently, an OCT device that can obtain signals at a high speed can be easily provided.

First Embodiment

An imaging device according to the first embodiment is Michelson type interferometer. In this case, optical filter is disposed at location where light has not yet been dispersed.

The first embodiment of the present invention will hereunder be described with reference to FIGS. 1A and 1B.

Figure 1C:
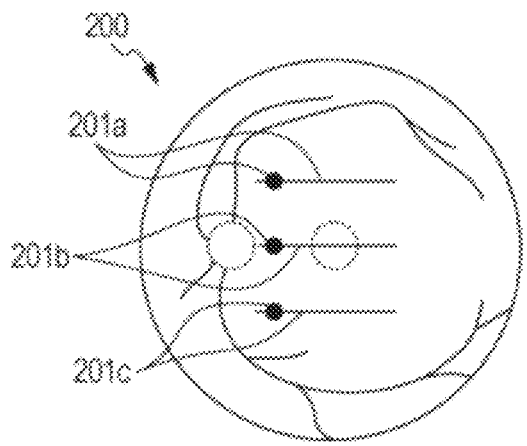
FIG. 1C is schematic view illustrating, for example, the structure of the imaging device using optical coherence tomography according to the first embodiment.

In the embodiment, as a basic structure, the imaging device using optical coherence tomography shown in FIG. 1A will be used. In the embodiment, the retina of an eye is an examination object 120 used as a measurement object. As the low-coherence light source 101, an SLD light source having an output of 20 mW, a center wavelength of 840 nm and a wavelength width of 45 nm is used. Light emitted from the SLD light source 101 is equally split into three lights by a 1-to-3 fiber beam splitter 102. The lights are branched into measuring lights and reference lights by three 50:50 fiber couplers 103. The measuring lights are formed into parallel beams by three fiber collimators 104. Then, by a scanning optical system 105 (formed by a galvano scanner and a scan lens) and the objective lens 106 (serving as an illumination optical system), the retina 120 of the eye is irradiated with the parallel beams. As shown in FIG. 1C, the beams are set so as to scan three different positions 201a, 201b, and 201c of the fundus 200. Returning lights, formed by reflection or scattering of the lights by the retina 120, pass through the same optical system again, and return to the fiber couplers 103.

The reference lights exit from three fiber collimators 107, are reflected by a reference mirror 109, and return to the fiber couplers 103. Here, for adjustment of a wavelength scattering amount with respect to the reference lights, the reference lights pass through a BK7 glass 108. The measuring lights that have been scattered by the retina 120 and that have returned to the fiber couplers 103 and the reference lights that have been reflected by the reference mirror 109 and that have returned to the fiber couplers 103 are combined with each other at the fiber couplers 103, so that interference lights are formed. A spectroscope 110, which is an interference-signal detecting device, disperses and detects the interference lights for respective wavelengths.

Figure 2A:
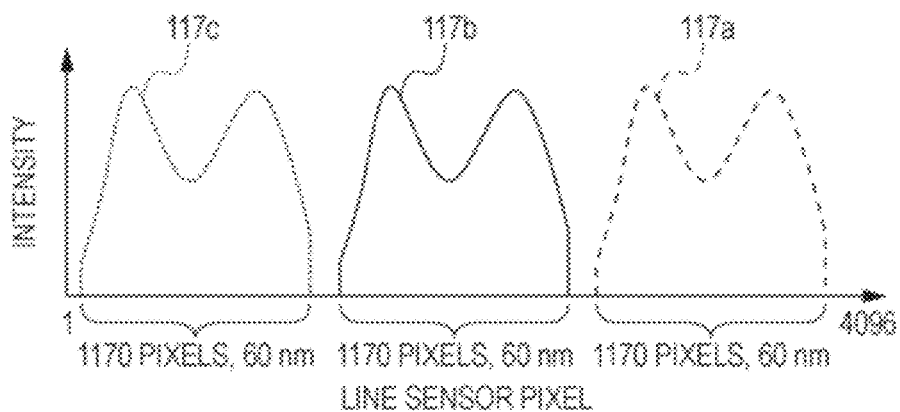
FIG. 2A is a schematic view of interference signal spectra according to the first embodiment.

The spectroscope 110 has the structure shown in FIG. 1B. The interference lights input by the fibers exit into the air from fiber ends 111 arranged at a certain interval, pass through a band-pass filter 112 (that passes only light having wavelengths in a wavelength range of from 810 nm to 870 nm, that is, light within a wavelength width of 60 nm), and are formed into parallel lights by a collimator lens 113. The parallel lights are dispersed by a 1200/mm transmission diffraction element 114, and are focused on a line sensor 116 having a pixel size of 10 [micro]m, having 4096 pixels, and having a line read-out period of 70 kHz by a focusing lens 115. Lenses in the spectroscope are selected so that the wavelengths of 810 nm to 870 nm are dispersed for 1170 pixels of the line sensor. When interference signals corresponding to the beams are measured with the spectroscope set in this way, graphs in a schematic view shown in FIG. 2A are generated. (Here, for simplicity, the interference signals are schematically drawn with simple lines while ignoring signals of small periods of the interference signals.) Of the wavelength spectrum of the light source, lights having wavelengths in the range of from 810 nm to 870 nm illuminate the line sensor and are detected by the line sensor.

Figure 3A:
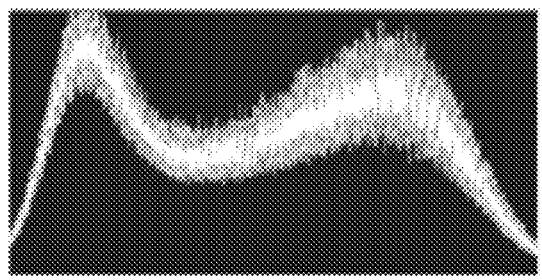
FIG. 3A shows an interference-signal wavelength spectrum according to the first embodiment.
Figure 3B:
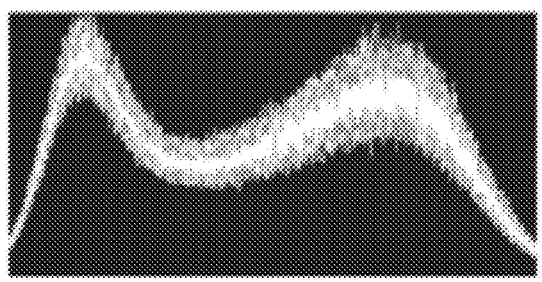
FIG. 3B shows an interference-signal wavelength spectrum according to the first embodiment.
Figure 3C:
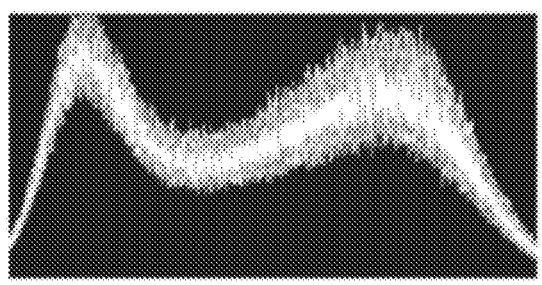
FIG. 3C shows an interference-signal wavelength spectrum according to the first embodiment.

In the above-described structure, when the retina is measured, as shown in FIGS. 3A to 3C, the wavelength spectra of the interference signals 117a, 117b, and 117c corresponding to the three measurement beams 201a, 201b, and 201c is measured. When signal processing including a Fourier transformation processing operation is performed on the basis of data of the measurement, three OCT images are obtained as shown in FIG. 4.

Figure 2B:
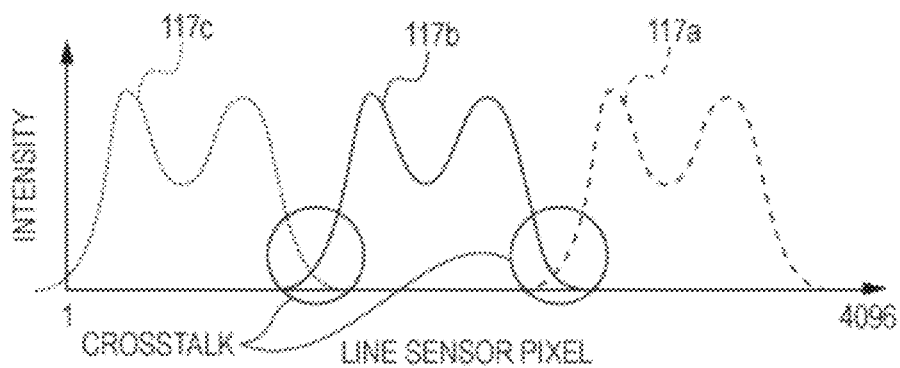
FIG. 2B is a schematic view of interference signal spectra when an optical filter is not provided.
Figure 3D:
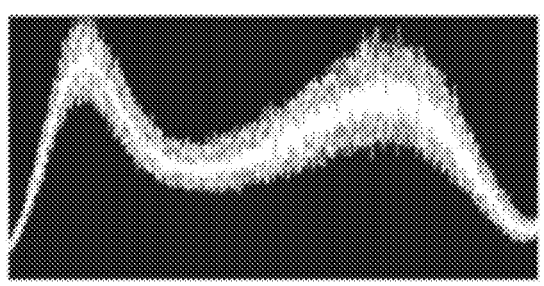
FIG. 3D shows a wavelength spectrum when an optical filter is not provided.
Figure 4A:
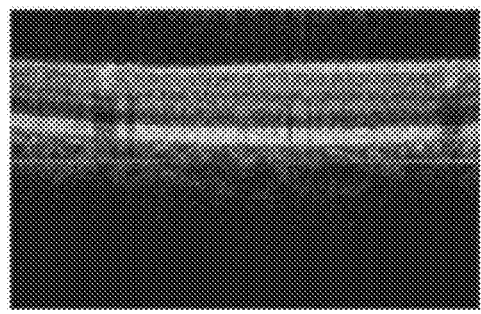
FIG. 4A shows an OCT image according to the first embodiment.
Figure 4B:
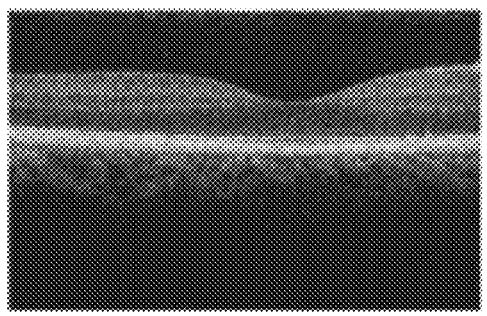
FIG. 4B shows the OCT image according to the first embodiment.
Figure 4C:
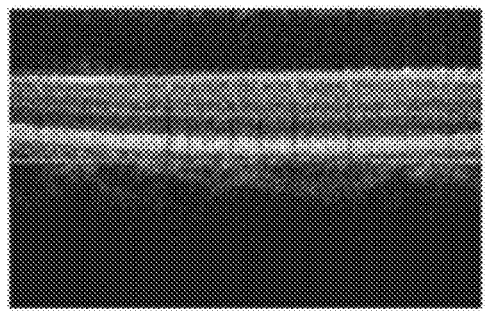
FIG. 4C shows the OCT image according to the first embodiment.
Figure 4D:
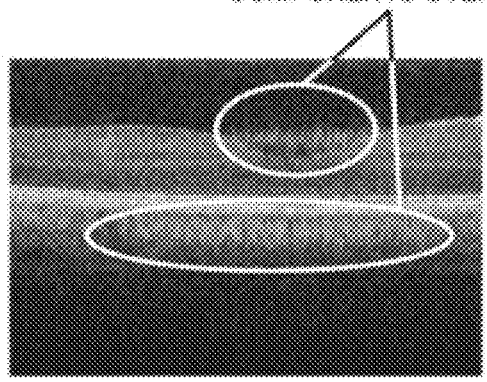
FIG. 4D shows an OCT image when an optical filter is not provided.

When the interference lights do not pass through the band-pass filter 112, the wavelength spectra of the interference signals detected by the spectroscope are such that crosstalk occurs between adjacent beams as shown in FIG. 2B. The interference signals in this state are as shown in FIG. 3D. Signal intensity at the right end of FIG. 3D is larger than signal intensities at the right ends of FIGS. 3A to 3C. This is caused by the influence of crosstalk. When the interference signals, which influence the crosstalk, are converted into OCT images, as shown in FIG. 4D, an unclear image that is superimposed by a portion of another beam image as a noise component is formed. To avoid this, if a method according to the present invention is not used, it is necessary to separate the spectra of the respective beams from each other so that crosstalk does not occur between adjacent interference signals. However, this requires the use of a line sensor having a larger number of pixels, thereby increasing costs and slowing down the read-out period.

Accordingly, according to the embodiment, OCT images, formed by a plurality of beams, are such that measuring signals for forming tomographic images having reduced noise components can be obtained at a high speed with a sensor array having a minimum number of pixels. According to the embodiment, the plurality of interference lights can be brought close to each other so as not to be superimposed upon each other on the sensor and so that noise components do not stand out when the interference lights are displayed as tomographic images.

Although, in the embodiment, the structure in which the band-pass filter 112 is inserted as the optical filter is described, similar effects can be provided if optical filters that limit the wavelengths of light reaching the line sensor 116 are used. For example, a short-pass filter that passes only short wavelengths, a long-pass filter that passes only long wavelengths, or a notch filter that does not pass particular wavelengths may also be used. Alternatively, any combination of these optical filters may be used. In addition, as methods of producing the optical filter, any method that is not an absorption type, a reflecting type, or an interference type based on a dielectric multilayer film may be used.

Further, although, in the embodiment, the case in which the insertion position of the optical filter 112 is in the spectroscope is described, similar effects may be obtained even if the optical filter 112 is inserted at any location where light has not yet impinged upon the sensor array 116. As in the embodiment, when the optical filter is disposed in the spectroscope, the optical system can be reduced in size.

Second Embodiment

An imaging device according to the Second embodiment is Michelson Type Interferometer. In this case, optical filter is disposed at location where light has not yet been split into reference lights and measuring lights.

As a second embodiment, a structure in which the position of the optical filter 112 is changed by using a bulk optical system (system where light passes through the air) is used instead of the optical fiber in the imaging device using optical coherence tomography in the first embodiment.

Figure 5A:
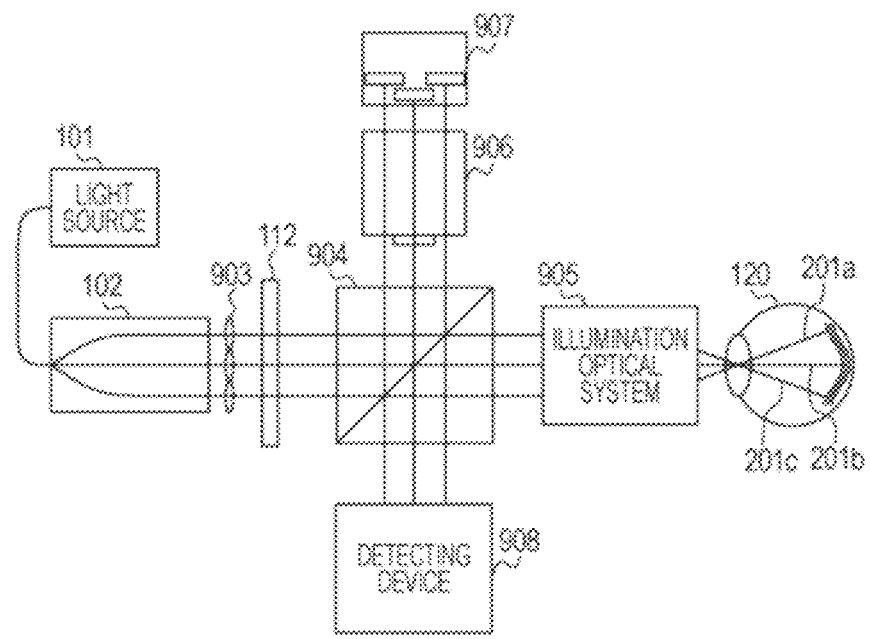
FIG. 5A is a schematic view illustrating the structure of an imaging device using optical coherence tomography according to a second embodiment.

FIG. 5A illustrates the structure of an imaging device using optical coherence tomography to which a bulk optical system is applied according to the second embodiment. In FIG. 5A, component parts having the same structures as those of the component parts shown in FIG. 1A are given the same reference numerals, so that common portions will not be described below.

In FIG. 5A, reference numeral 903 denotes a collimate lens array, reference numeral 904 denotes a cube beam splitter, reference numeral 905 denotes an illumination optical system, reference numeral 906 denotes a dispersion compensation glass, reference numeral 907 denotes a reference mirror, and reference numeral 908 denotes an interference-signal detecting device.

In the embodiment, an optical system that is provided at a location where light from a light source has already been equally split into three beams by a 1-to-3 fiber beam splitter 102 is formed by a bulk optical system. First, the collimate lens array 903 collimates the beams into parallel beams. The three beams pass through a band-pass filter 112, and is split into measuring lights and reference lights by the 50:50 cube beam splitter 904. The three measuring lights are focused on a retina 120 by the illumination optical system including an eyepiece, a galvano scanner, and a scan lens. The three beams are adjusted so as to scan portions represented by line segments and the respective beam spots 201a, 201b, and 201c shown in FIG. 1C. Lights that are scattered from a focusing point of the three beams are guided to the cube beam splitter 904 through the illumination optical system 905, and are combined with the reference lights. In contrast, the reference lights pass through the dispersion compensation glass 906, are reflected by the reference mirror 907, and return to the cube beam splitter 904.

The reference lights and the measuring lights that have returned to the cube beam splitter 904 are combined, and become interference lights. The interference lights are guided to the interference-signal detecting device 908. The interference-signal detecting device 908 has a structure corresponding to that of the spectroscope shown in FIG. 1A that does not include the band-pass filter 112. Even in the structure according to this embodiment, the advantages of the band-pass filter 112 are provided, so that, as in FIG. 2A, there is no crosstalk between interference signals detected by a line sensor 116.

Accordingly, even if the optical filter 112 for limiting the wavelengths of the lights reaching the line sensor 116, such as a band-pass filter, is inserted at a location where the lights have not yet been split into the measuring lights and the reference lights, the advantages of the present invention are provided. In this case, since unnecessary wavelength components do not mix with the measuring lights, scattering light noise generated by the unnecessary wavelengths is reduced. Even if, as in the first embodiment, the optical filter 112 is inserted at a location where the interference signals have already been combined, that is, between the cube beam splitter 904 and the interference-signal detecting device 908, similar advantages can be obtained.

Third Embodiment

An imaging device according to the Third embodiment is Michelson Type Interferometer. In this case, different optical filters are disposed for respective beams.

As a third embodiment, a structure in which separate light sources are provided for respective beams is described instead of the structure in which one low-coherence light source 101 branches light into a plurality of beams as in the imaging device making use of optical coherence tomography according to the first and second embodiments.

Figure 5B:
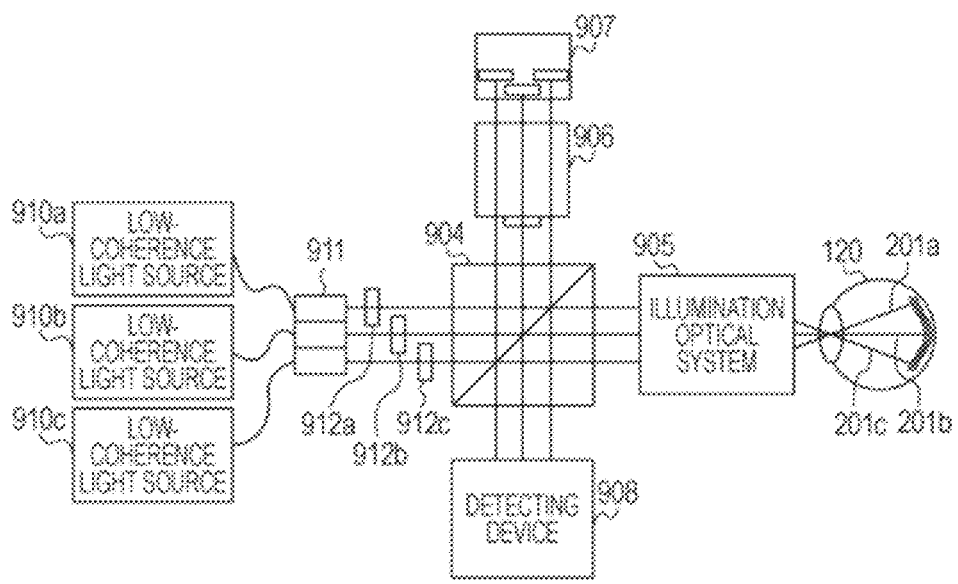
FIG. 5B is a schematic view illustrating the structure of an imaging device using optical coherence tomography according to a third embodiment.

FIG. 5B illustrates the structure of an imaging device using optical coherence tomography to which a bulk optical system is applied according to the third embodiment. In FIG. 5B, component parts having the same structures as those of the component parts shown in FIG. 1A are given the same reference numerals, so that common portions will not be described below.

In FIG. 5B, reference numerals 910a, 910b, and 910c denote low-coherence light sources, reference numeral 911 denotes a fiber collimator array, and reference numerals 912a, 912b, and 912c denote optical filters.

In the embodiment, the low-coherence light sources 910a, 910b, and 910c corresponding to beams 201a, 201b, and 201c that scan a retina are provided. The structure of the imaging device according to the third embodiment is the same as that of the imaging device using optical coherence tomography to which a bulk optical system is applied according to the second embodiment except that lights from the respective light sources are collimated into parallel beams by the fiber collimator array 911 and that the parallel lights pass through the respective optical filters 912a, 912b, and 912c.

Figure 2C:
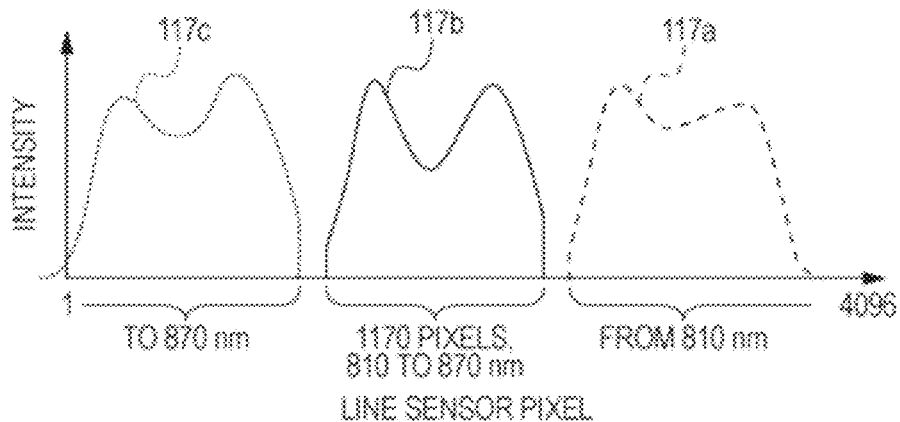
FIG. 2C is a schematic view of interference signal spectra according to a third embodiment.

FIG. 2C is a schematic view of wavelength spectra of interference signals corresponding to the respective beams in the embodiment. The shapes of the wavelength spectra of the respective light sources differ from each other due to manufacturing spread. As in the first embodiment, SLD light sources having an output of 20 mW, a center wavelength of 840 nm and a wavelength width of 45 nm are used. The optical filter 912a is a long-pass filter that passes wavelengths greater than or equal to 810 nm therethrough. The optical filter 912b is a band-pass filter that passes wavelengths of from 810 nm to 870 nm therethrough. The optical filter 912c is a short-pass filter that passes wavelengths less than or equal to 870 nm therethrough. Therefore, as shown in FIG. 2C, it is possible to obtain wavelength spectra that do not include crosstalk, and, as in the first and second embodiments, to obtain at a high speed OCT images by a plurality of beams with a sensor array having a minimum number of pixels. In the embodiment, it is possible to select an optimal optical filter in accordance with, for example, wavelength spectral characteristics of the individual beams and detection positions on the sensor array.

Although, in the above-described first to third embodiments, the use of three measuring beams is exemplified, the present invention is effective for any case in which two or more measuring beams are used. In addition, although a one-dimensional line sensor is exemplified as a sensor array that detects interference signal spectra, similar advantages are also obtained when a two-dimensional sensor array or a plurality of sensor arrays are used.

Fourth Embodiment

An imaging device according to the Fourth embodiment is Mach-Zehnder Type Interferometer. In this case, intercepting member is disposed at a location where light has already been dispersed.

Although, in the previous embodiments, a Michelson type interferometer is used, an exemplary structure in which a Mach-Zehnder type interferometer is used will be described in a fourth embodiment.

Figure 6A:
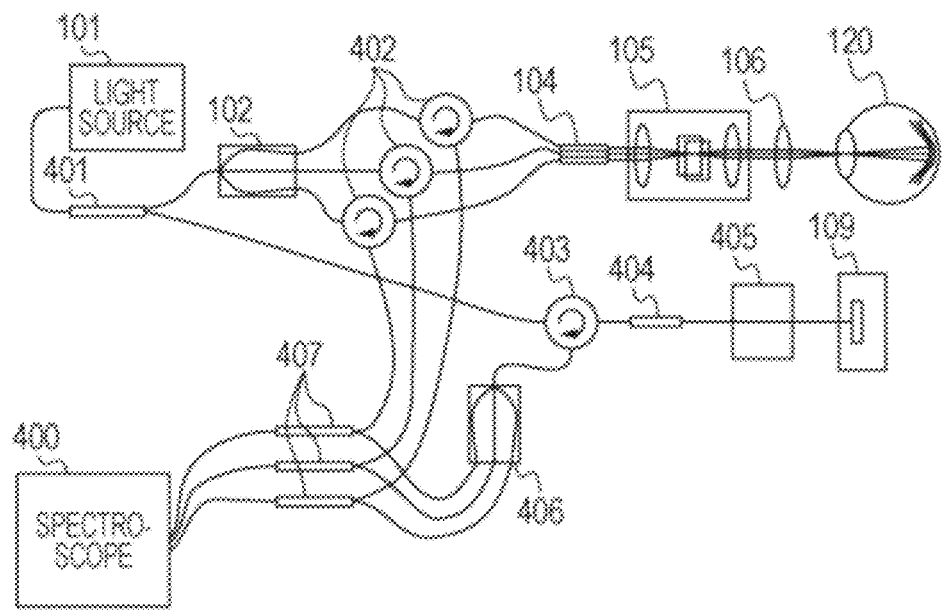
FIG. 6A is a schematic view illustrating the structure of an imaging device using optical coherence tomography according to a fourth embodiment.
Figure 6B:
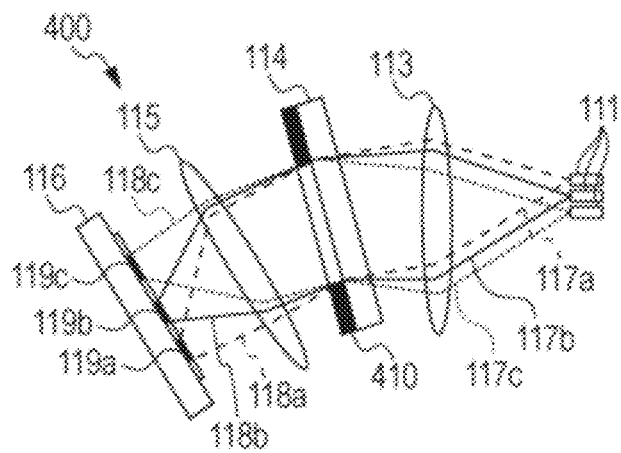
FIG. 6B is a schematic view illustrating the structure of the imaging device using optical coherence tomography according to the fourth embodiment.

FIGS. 6A and 6B are schematic views illustrating the structure of an imaging device using optical coherence tomography to which a Mach-Zehnder type interferometer is applied according to the fourth embodiment. In FIGS. 6A and 6B, component parts having the same structures as those of the component parts shown in FIGS. 1A and 1B are given the same reference numerals, so that common portions will not be described below.

Light generated from an SLD light source 101 is branched into measuring light and reference light by a 1-to-2 fiber beam splitter 401. The measuring light is equally split in three by a 1-to-3 fiber beam splitter 102, and the three beams are input to respective optical circulators 402. The lights that have passed through the respective optical circulators 402 are collimated into parallel beams by three fiber collimators 104. Then, as in the first embodiment, an objective lens 106 and an illumination optical system 105 including a galvano scanner and a scan lens cause the parallel lights to illuminate a retina 120 of an eye.

Returning lights, formed by reflection or scattering of the lights at the retina 120, pass through the same optical system and return to the optical circulators 402. The lights that have returned to the optical circulators 402 are output to 2-to-1 fiber couplers 407 instead of to the fiber beam splitter 102. The reference lights pass through an optical circulator 403, exit from a fiber collimator 404, pass through a dispersion compensation glass 405, is reflected by a reference mirror 109, and returns to the optical circulator 403. The reflected light that has returned to the optical circulator 403 is output to a 1-to-3 fiber beam splitter 406 by the optical circulator 403, and is equally split in three. The split lights are input to 2-to-1 fiber couplers 407.

The three measuring lights, scattered by the retina 120 and input to the 2-to-1 fiber couplers 407, and the three equally split reference lights, input to the 2-to-1 fiber couplers 407, are combined with each other at the 2-to-1 fiber couplers 407, and become interference lights. A spectroscope 400, serving as an interference-signal detecting device, disperses and detects the interference lights for respective wavelengths.

The spectroscope 400 has the structure shown in FIG. 6B. The structure of the spectroscope 400 is the same as that of the spectroscope 110 in the first embodiment except that an aperture 410 is inserted behind a transmission diffraction grating 114. The aperture 410 has a circular hole formed in an aluminum plate subjected to black alumite treatment. Light that has passed through the transmission diffraction grating 114 exits from the transmission diffraction grating 114 at angles that differ for respective wavelengths. The size of the circular hole of the aperture 410 is adjusted so that light having wavelengths less than or equal 810 nm and light having wavelengths greater than or equal to 870 nm are intercepted. Therefore, as in FIGS. 3A to 3C in the first embodiment, wavelength spectra of interference signals 117a, 117b, and 117c are measured. When signal processing including a Fourier transformation processing operation is performed on the basis of data thereof, three OCT image are obtained as shown in FIG. 4. Here, although an aluminum plate subjected to black alumite treatment is used as the aperture, as long as members that do not pass predetermined lights, such as those made of metal, wood, or paper, are used, the advantages of the present invention can be provided. Even in the fourth embodiment, as in the first embodiment, the optical filter 112 may be used instead of the aperture 410. Alternatively, in the first embodiment, the aperture 410 may be used instead of the optical filter 112.

According to the embodiment, the advantages of the present invention can be provided regardless of the form of an interferometer or even when, instead of an optical filter, a light intercepting member is used as an adjusting member for adjusting light quantity.

Fifth Embodiment

Optical Filter is Disposed in Reference-Light Optical Path

As a fifth embodiment, an exemplary structure in which an optical filter is disposed in a reference-light optical path is described.

Figure 7A:
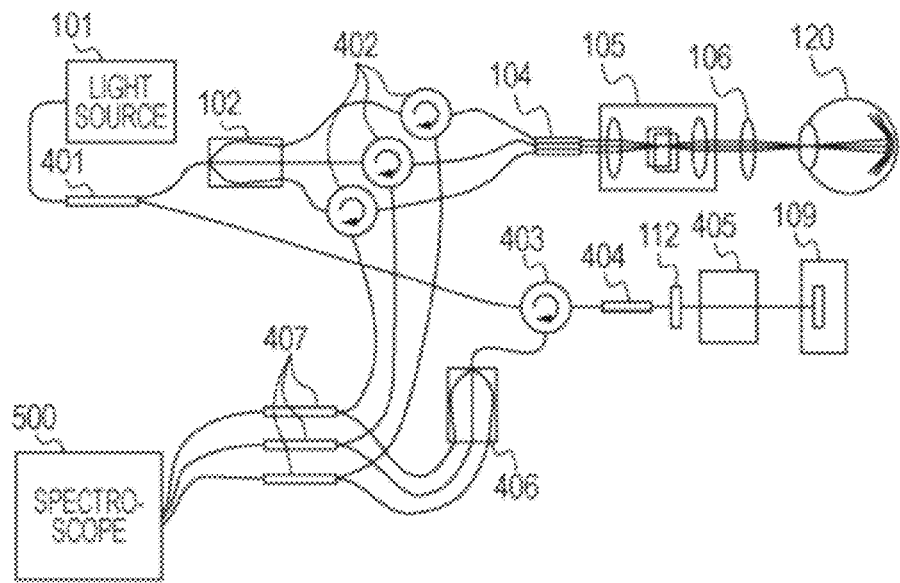
FIG. 7A is a schematic view illustrating the structure of an imaging device using optical coherence tomography according to a fifth embodiment.
Figure 7B:
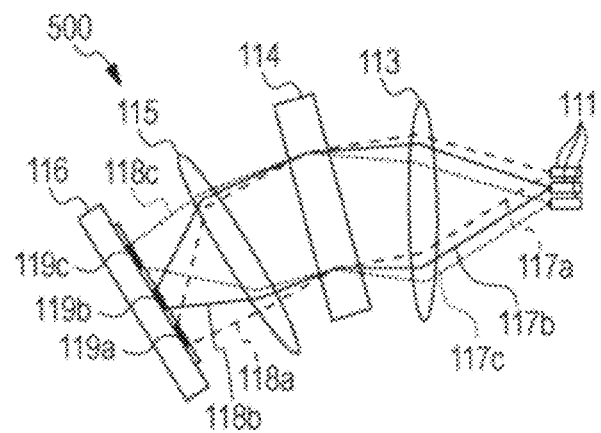
FIG. 7B is a schematic view illustrating the structure of the imaging device using optical coherence tomography according to the fifth embodiment.

FIGS. 7A and 7B are schematic views illustrating the structure of an imaging device using optical coherence tomography in which an optical filter is disposed in a reference-light optical path according to the fifth embodiment.

In FIGS. 7A and 7B, component parts having the same structures as those of the component parts shown in FIGS. 1A and 1B and FIGS. 6A and 6B are given the same reference numerals, so that common portions will not be described below.

The imaging device shown in FIG. 7 differs from that in FIG. 6 in that an optical filter 112 is disposed in a reference-light optical path and in that a spectroscope 500 has a different structure. The optical filter 112 has the same characteristics as those of the optical filter 112 described in the first embodiment. As shown in FIG. 7B, the spectroscope 500 has a structure corresponding to the spectroscope 110 described in the first embodiment that does not include the optical filter 112.

In the structure according to the embodiment, the optical filter 112 does not influence measuring lights and returning lights. Therefore, lights other than those having wavelengths of from 810 nm to 870 nm included in returning lights returning from a retina 120 of an eye are mixed in combined lights at fiber couplers 407. However, the reflectivity at the retina 120 of the eye is approximately 0.001% (−50 dB), so that the light quantity of the lights having such wavelengths can be ignored with respect to the light quantity of reference lights. Therefore, since the amount of crosstalk on a line sensor 116 can be essentially ignored, it is possible to bring the plurality of interference lights close to each other on the sensor so as to prevent them from being superimposed upon each other to the extent possible.

By providing the optical filter 112 in the optical path of reference lights, the returning light quantity is not lost by the optical filter. Therefore, since the returning lights are efficiently used in the combined lights, it is possible to obtain a relatively high quality tomographic image.

Accordingly, even when the optical filter 112 is disposed in a measuring-light optical path, the advantages of the present invention are obtained. Although, in the embodiment, a Mach-Zehnder type interferometer is used as an example, a similar structure is possible even for other types of interferometers such as a Michelson type interferometer.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-124273, filed May 22, 2009, and Japanese Patent Application No. 2010-066729, filed Mar. 23, 2010, which are hereby incorporated by reference herein in their entirety.

The invention claimed is:

1. An imaging apparatus comprising:
an illuminating unit configured to illuminate an object with first and second measuring lights;
a detecting unit configured to detect by wavelength first and second combined lights formed by combining first and second returning lights and first and second reference lights corresponding to the first and second measuring lights, the first and second returning lights returning from the object illuminated by the first and second measuring lights;
a reducing unit configured to reduce a light quantity of a light of a specific wavelength so as to reduce superimposition of the first and second combined lights upon each other at the detecting unit; and
an obtaining unit configured to obtain an optical coherence tomographic image of the object based on the first and second combined lights whose superimposition is reduced.

2. The imaging apparatus according to claim 1, wherein the detecting unit includes:
a dispersing element configured to disperse by wavelength the first and second combined lights; and
a sensor configured to detect the first and second lights by wavelength dispersed by the dispersing element, and
wherein the reducing unit reduces the superimposition of the first and second lights on the sensor.

3. The imaging apparatus according to claim 2, wherein the detecting unit includes a focusing unit that focuses the first and second lights on a first area and a second area, respectively, and
wherein the reducing unit reduces a light quantity of light of the first light having a wavelength capable of illuminating the second area.

4. The imaging apparatus according to claim 2, wherein the reducing unit is an intercepting member that intercepts a light of a specific wavelength in the first and second lights dispersed at the dispersing element.

5. The imaging apparatus according to claim 1, further comprising a light source configured to generate light, a splitting unit configured to split the light from the light source into reference light and measuring light, and a scanning unit configured to perform scanning using the first and second measuring lights based on the object.

6. The imaging apparatus according to claim 5, wherein the splitting unit is configured to combine the reference light and the measuring light, and
wherein the light generated from the light source is split into a plurality of lights, the plurality of split lights are split into reference lights and measuring lights, and the scanning unit scans the first and second measuring lights on the object.

7. The imaging apparatus according to claim 6, wherein the reducing unit is provided on an optical path from the light source to the splitting unit, and the superimposition is reduced by selectively reducing a light quantity of the light of a specific wavelength from the light source.

8. The imaging apparatus according to claim 6, further comprising:
a plurality of light sources,
wherein the splitting unit is configured to split a plurality of lights generated by the plurality of light sources into the first and second reference lights and the first and second measurement lights, and the scanning unit is configured to scan the object with the first and second measurement lights.

9. The imaging apparatus according to claim 5, comprising a plurality of the light sources, wherein lights are generated from the plurality of the light sources, the generated lights are split into reference lights and measuring lights, and the measuring lights scan the object.

10. The imaging apparatus according to claim 5, further comprising a combining unit configured to combine the reference light and the measuring light,
wherein the light generated from the light source is split into the measuring light and the reference light, the split measuring light and reference light are each split into a plurality of lights, and the scanning unit scans the first and second measuring lights on the object.

11. The imaging apparatus according to claim 1, wherein the reducing unit is provided in at least one of an optical path extending from a light source to a splitting unit, an optical path of the first and second combined lights, and an optical path of first and second reference lights.

12. The imaging apparatus according to claim 1, wherein the reducing unit is an optical filter that limits transmittance or reflectivity of light having a particular wavelength.

13. The imaging apparatus according to claim 1, wherein the reducing unit is provided on an optical path of the first and second reference lights, and the superimposition is reduced by selectively reducing a light quantity of the first and second reference lights of a specific wavelength.

14. The imaging apparatus according to claim 1, wherein the reducing unit is provided on an optical path of the first and second combined lights, and the superimposition is reduced by selectively reducing a light quantity of the first and second combined lights of a specific wavelength.

15. The imaging apparatus according to claim 1, wherein the object is a subject's eye.

16. The imaging apparatus according to claim 1, further comprising:

a combining unit configured to combine the first and second reference lights and the first and second measuring lights, wherein the splitting unit is configured to split the light from the light source into reference light and measuring light, split the measuring light into the first and second measuring lights, and split the reference light into the first and second reference lights, and wherein the scanning unit is configured to scan the object with the first and second measuring lights.

17. An imaging method comprising the steps of:

illuminating an object with first and second measuring lights;

detecting by wavelength first and second combined lights formed by combining first and second returning lights and first and second reference lights corresponding to the first and second measuring lights, by a detecting unit, the first and second returning lights returning from the object illuminated by the first and second measuring lights;

reducing a light quantity of a specific wavelength so as to reduce superimposition of the first and second combined lights upon each other at the detecting unit; and obtaining an optical coherence tomographic image of the object based on the first and second combined lights whose superimposition is reduced.

18. A non-transitory computer readable medium having program code stored thereon for causing a computer to execute the imaging method according to claim 17.

19. The imaging method according to claim 17, wherein, in the reducing step, the superimposition is reduced by selectively reducing a light quantity of the first and second reference lights of a specific wavelength.

20. The imaging method according to claim 17, wherein, in the reducing step, the superimposition is reduced by selectively reducing a light quantity of the first and second combined lights of a specific wavelength.

21. An imaging apparatus comprising:

a detecting unit configured to detect by wavelength first and second combined lights based on returning light returning from an object illuminated by measuring light;

a reducing unit configured to reduce a light quantity of a light of a specific wavelength so as to reduce superimposition of the first and second combined lights upon each other at the detecting unit; and an obtaining unit configured to obtain an optical coherence tomographic image of the object based on the first and second combined lights whose superimposition is reduced.

22. The imaging apparatus according to claim 21, wherein the detecting unit includes:

a dispersing element configured to disperse by wavelength the first and second combined lights; and a sensor configured to detect the first and second lights by wavelength dispersed by the dispersing element, wherein the reducing unit reduces the superimposition of the first and second lights on the sensor.

23. The imaging apparatus according to claim 22, wherein the detecting unit includes a focusing unit that focuses the first and second lights on a first area and a second area, respectively, and wherein the reducing unit reduces a light quantity of light of the first light having a wavelength capable of illuminating the second area.

24. The imaging apparatus according to claim 22, wherein the reducing unit is an intercepting member that intercepts a light of a specific wavelength in the first and second lights dispersed at the dispersing element.

25. The imaging apparatus according to claim 21, wherein the reducing unit is provided in an optical path of the first and second combined lights.

26. The imaging apparatus according to claim 21, wherein the reducing unit is an optical filter that limits transmittance or reflectivity of light having a particular wavelength.

27. The imaging device according to claim 21, wherein the reducing unit is provided on an optical path of the first and second combined lights, and the superimposition is reduced by selectively reducing a light quantity of the first and second combined lights of a specific wavelength.

28. An imaging method comprising the steps of:

detecting by wavelength first and second combined lights based on returning light returning from an object illuminated by measuring light, by a detecting unit;

reducing a light quantity of a specific wavelength so as to reduce superimposition of the first and second combined lights upon each other at the detecting unit; and obtaining an optical coherence tomographic image of the object based on the first and second combined lights whose superimposition is reduced.

29. A non-transitory computer readable medium having program code stored thereon for causing a computer to execute the imaging method according to claim 28.

30. The imaging method according to claim 28, wherein, in the reducing step, the superimposition is reduced by selectively reducing a light quantity of the first and second combined lights of a specific wavelength.

* * * * *